United States Patent [19]

Greenquist

[11] Patent Number: 4,806,311
[45] Date of Patent: Feb. 21, 1989

[54] MULTIZONE ANALYTICAL ELEMENT HAVING LABELED REAGENT CONCENTRATION ZONE

[75] Inventor: Alfred C. Greenquist, Elkhart, Ind.

[73] Assignee: Miles Inc., Elkhart, Ind.

[21] Appl. No.: 770,076

[22] Filed: Aug. 28, 1985

[51] Int. Cl.⁴ .............. G01N 31/22; G01N 33/53; G01N 33/563

[52] U.S. Cl. .................. 422/56; 422/57; 422/58; 435/7; 435/805; 436/807; 436/810; 436/815

[58] Field of Search ........ 436/807, 810, 815; 422/56, 57, 58; 435/7, 805

[56] References Cited

U.S. PATENT DOCUMENTS

| | | | |
|---|---|---|---|
| 3,904,373 | 9/1975 | Harper | 436/169 X |
| 4,235,601 | 11/1980 | Deutsch et al. | 436/810 |
| 4,258,001 | 3/1981 | Pierce et al. | 422/56 |
| 4,289,747 | 9/1981 | Chu | 435/7 X |
| 4,446,232 | 5/1984 | Liotta | 422/56 X |
| 4,459,358 | 7/1984 | Berke | 436/170 |
| 4,468,470 | 8/1984 | Aalberse | 426/815 X |
| 4,496,654 | 1/1985 | Katz et al. | 422/56 X |
| 4,517,288 | 5/1985 | Giegel et al. | 435/7 |
| 4,530,900 | 7/1985 | Marshall | 435/7 |
| 4,551,307 | 11/1985 | Koyama et al. | 422/56 |
| 4,567,136 | 1/1986 | Okaniwa et al. | 422/56 X |
| 4,649,123 | 3/1987 | Charlton et al. | 436/74 X |
| 4,670,381 | 6/1987 | Frickey et al. | 422/56 X |

FOREIGN PATENT DOCUMENTS

0066648 12/1982 European Pat. Off.

Primary Examiner—Benoit Castel
Assistant Examiner—Jill Johnston
Attorney, Agent, or Firm—Daniel W. Collins

[57] ABSTRACT

A multizone test device for the determination of analyte from a liquid test medium upon contact with the liquid test medium and a labeled reagent comprising a chemical group having a detectable physical property. The test device preferably comprises multilayers including a reagent layer incorporated with an immobilized reagent and a detection layer incorporated with an immobilized form of a binding substance for the labeled reagent. The immobilized reagent and the labeled reagent comprise specific binding partners which will bind to each other dependent upon the amount of analyte present. Labeled reagent which does not become bound to the immobilized reagent in the reagent layer migrates into the detection layer and becomes bound to and immobilized by the immobilized binding substance therein. As a result, reverse migration of the labeled reagent into the reagent layer is prevented and the detectable physical property provided by the label of the labeled reagent is localized in the detection layer for the precise measurement thereof and correlation to the amount of analyte in the test medium.

33 Claims, 2 Drawing Sheets

MULTIZONE ANALYTICAL ELEMENT HAVING LABELED REAGENT CONCENTRATION ZONE

BACKGROUND OF THE INVENTION

1. Field of the Invention

The present invention relates to multizone analytical elements which are useful for the determination of an analyte in a liquid test medium. In particular, the present invention relates to multilayer immunoassay test devices involving the use of labeled reagents comprising a chemical group having a detectable physical property such as fluorescence or color.

2. Description of the Prior Art

Multizone analytical elements or test devices have been previously proposed and have been applied to binding assays, e.g., immunoassays, which depend upon the ability of an antibody or antigen to bind to a specific analyte for the determination of the analyte in the liquid test medium. Such assays include those immunoassays where a labeled reagent, such as a labeled form of the analyte or an antibody thereto, participates in an antigen-antibody reaction to form a free species and a bound species thereof such that the amount of the labeled reagent in one of such species can be correlated to the amount of analyte in the liquid test medium. In principle, such assays are referred to as heterogeneous immunoassays because the free and bound species must be separated in order to complete the assay.

Multizone, particularly multilayer, analytical elements are now known in the art which inherently perform the required separation step so that no additional manipulations are needed after application of the liquid test medium. In general, such devices include a plurality of layers having the necessary reagents for carrying out an immunoassay and for accomplishing the necessary separation step incorporated therein. A number of such devices further include a detection layer from which the signal produced by a labeled reagent in either the bound or free species is detected and measured. Detectable signals provided by such devices are usually optical in nature such as color changes, fluorescence, or the like. Alternatively, detection can be accomplished by electrochemical measurements using, for example, potentiometric or ampometric techniques.

For example, such multilayer immunoassay analytical elements are described by European Patent Publication No. 97,952 and German Publication No. DE-OS No. 3329728 where an immobilized form of a binding partner, such as an immobilized antibody to an antigen, and an antigen labeled with a detectable substance are incorporated therein. Upon the application of a liquid test medium to such device, antigen from the test medium competes with labeled antigen incorporated into the device for binding to the immobilized antibody. Separation of the bound species from the free species occurs upon migration of the free species of the labeled antigen away from the immobilized zone.

Similarly, European Patent Publication Nos. 51,183 and 66,648 disclose such devices where the determination of antigen or antibody in a liquid test medium is dependent upon the competitive binding of the antigen (or antibody) with a labeled form of the antigen (or antibody) for an immobilized form of a binding partner thereof, such as immobilized antibody (or antigen).

Other multilayer immunoassay test devices have also been proposed, such as described in U.S. Pat. No. 4,258,001, which include one or more layers comprising particulate, three-dimensional lattices formed by a plurality of organopolymeric particles. The particles form interconnected void spaces which are claimed to provide for the transport of high molecular weight analytes therethrough. Although not required, it is suggested that interactive compositions, such as antigens or antibodies, can be immobilized onto the particles by providing active linking or binding sites on the particles to which such interactive compositions can be covalently bonded.

Another of such devices is described in U.S. Pat. No. 4,446,232 which is based on the principle of competition between bound and free species of analyte for a fixed number of recognition sites on an enzyme-labeled antibody. The determination of analyte in a test sample depends upon the binding of the analyte to enzyme-labeled antibodies in one zone of the device and which then pass into another zone of the device where the enzyme activity of the enzyme-linked antibodies bound to analyte is detected. One of the zones further includes bound and immobilized analyte which competes with analyte from the test sample for binding to the enzyme-labeled antibodies and which bind and immobilize any of the enzyme-labeled antibodies which do not become bound to analyte from the test sample.

A particular disadvantage, however, of such devices is that reverse fluid migration results in reaction products, which have migrated into the lower or detection layer, to migrate back up into the upper layers, resulting in chemical interferences and diminished test response. To overcome this disadvantage, analytical test devices have been proposed which attempt to localize or otherwise prevent such reverse fluid migration of the reaction products.

For example, European Patent Publication Nos. 51,183 and 66,648 suggest layers for collection of the detectable reaction product comprising hydrophilic high molecular weight substances. EP No. 66,648 further suggests the incorporation of mordanting agents in the detection layer which have a strong interaction with the detectable reaction product in order to collect the detectable reaction product therein. Such mordanting agents include cationic polymers, anionic polymers and quaternary salts.

Similarly, U.S. Pat. Nos. 4,144,306 and 4,042,335 disclose multilayer analytical elements which include a registration layer incorporated with a mordant for a detectable species in order to collect the detectable species therein and thereby prevent diffusion or migration of the detectable species out of the registration layer.

A variation of such devices is disclosed by U.S. Pat. No. 4,459,358 which describes a multilayer element comprising a spreading layer, a reaction layer incorporated with a diffusible labeled antibody, and a registration layer incorporated with materials adapted to non-specifically bind, immobilize or "mordant" antibodies, such as latex particles. Upon application of a liquid test medium to the device, analyte from the test medium associates with the labeled antibody in the reaction layer and immunoprecipitates therein. Any of the labeled antibody which does not become bound to the analyte diffuses into the registration layer where it is immobilized by the mordant incorporated therein.

However, the use of mordanting agents can interfere with the prerequisite reactions which are necessary for the formation or release of the detectable reaction product as a result of non-specific binding of the mordanting agent. Such interference can make both detection and measurement unreliable, as well as decrease the sensitivity of the test device.

In attempts to overcome the disadvantages of mordanting agents in a registration layer, other analytical elements have been proposed employing mordanting agents in a layer other than a registration layer in order to prevent the migration of a formed detectable reaction product into a layer other than a registration or detection layer which would otherwise render the detectable reaction product undetectable. Such a device is disclosed by U.S. Pat. No. 4,166,093 which includes a species migration-inhibiting layer interposed between a radiation-blocking layer and a reagent layer of a multilayer analytical element. The detectable species migration-inhibiting layer is permeable to analyte and fixes or otherwise prevents a significant portion of any detectable species, such as a dye formed in the reagent layer, from further migrating up into the radiation-blocking layer. Such detectable species migration-inhibiting layer comprises a mordant for the particular detectable species formed in the reagent layer. However, such an inhibiting layer still presents the disadvantage of a mordanting agent which may interfere with reactions initiated by the presence of analyte and prevent or substantially inhibit the formation or release of the detectable species.

Still another attempt to overcome the problem of reverse fluid migration in multilayer analytical elements is disclosed by International Publication No. WO 84/02193 which provides for a chromogenic support immunoassay which comprises collection of an immune complex comprising analyte bound to an enzyme-labeled anti-analyt antibody on a porous or microporous support material. The support functions to concentrate the chromatic signal generated by the label component upon reaction with signal generating reagents in the support material. Concentration of the chromatic signal results from covalent attachment of the reaction product to the support, and the problem of reverse fluid migration being overcome by providing a single layer. The immunoassay, however, requires a number of incubation and washing steps in order to localize and concentrate the signal on the support. Although the immunoassay overcomes reverse fluid migration by providing a single layer support within which the necessary reactions for production of the chromatic signal occur, it still presents the disadvantages of extensive incubation and washing steps which are not necessary with a multilayer analytical element.

Accordingly, it is an object of the present invention to overcome the aforementioned disadvantages by providing a specific binding assay in a multizone, or multilayer, test device which concentrates the detectable response of a labeled reagent without interfering with the specific binding reactions involved in the assay.

Another object of the present invention is to provide, in a multizone, or multilayer, test device, a specific binding assay having an end point in the assay where further migration of the detectable species does not occur.

Further, it is an object of the present invention to provide a sensitive specific binding assay for the highly accurate determination of analyte from a liquid test medium and which has substantially little or no background signal.

SUMMARY OF THE INVENTION

The present invention provides a multizone test device for the determination of analyte from a liquid test medium based on binding interactions among the analyte, a labeled reagent, and an immobilized binding substance for the labeled reagent. The test device comprises, in fluid flow contact, (1) a reagent zone incorporated with the immobilized reagent which will be an immobilized form of the analyte or a binding analog thereof, or an immobilized form of a binding partner of the analyte, depending on the immunoassay scheme used, and (2) a detection zone incorporated with an immobilized form of a binding substance for the labeled reagent. The labeled reagent is a form of a binding partner of the analyte, or a form of the analyte or a binding analog thereof, which is labeled with a chemical group having a detectable physical property and which further comprises a binding site for the immobilized binding substance in the detection zone.

The present invention derives its principal advantages from the use of a labeled reagent which has its own detectable property and which can be rendered immobilized in the detection zone by an inherent or introduced binding affinity. No separately migratable detectable species is generated as with prior art devices and immobilization and concentration of the response results from highly specific and strong binding interactions.

The immobilized reagent in the reagent zone and the labeled reagent are selected to comprise specific binding partners which will bind to one another dependent upon the amount of analyte present. When the labeled reagent is a labeled form of the analyte or an analog thereof, the immobilized reagent will be an immobilized form of a binding partner for the analyte, and the analyte and labeled reagent will compete for binding to the immobilized reagent. When the labeled reagent is a labeled form of a binding partner for the analyte, the immobilized reagent will be an immobilized form of the analyte or an analog thereof, and the labeled reagent that does not become bound to analyte will become immobilized by binding to the immobilized reagent. Whether labeled analyte or labeled binding partners are involved, a portion of the labeled reagent will remain or become unbound to the immobilized reagent dependent upon the amount of analyte present.

The resulting labeled reagent which remains or becomes free to migrate within and out of the reagent zone then passes into the detection zone where the binding site of the labeled reagent binds with the immobilized binding substance in the detection zone. The resulting immobilized labeled reagent is prevented from migrating from the detection zone up into the reagent zone and the detectable chemical group of the labeled reagent provides a detectable physical signal in the detection zone which is measured and correlated to the amount of analyte in the test medium.

DESCRIPTION OF THE PREFERRED EMBODIMENTS

The multizone test device of the present invention provides a specific binding assay in a zoned or layered test strip or device. The assay depends upon the partitioning of a labeled reagent, which is either applied to the device or incorporated within the device, between being retained in the reagent zone by being bound or immobilized to the immobilized reagent and being free to migrate into the detection zone. The present invention provides an advantageous means for concentrating the labeled reagent which migrates to the detection zone.

In order to simplify the disclosure hereinafter, the test device of the pesent invention will now be described principally as comprising a layered structure. It will be understood that other types of zones can accomplish the same result. Also, the labeled reagent will be selected to be a labeled form of a binding partner of the analyte and the immobilized reagent will be selected to be an immobilized form of the analyte (with immobilized analyte being replaceable by an immobilized form of an analog of the analyte as is. understood in the art).

In particular, the test device of the present invention comprises at least one reagent layer and a detection layer, and, as will be described in greater detail hereinafter, can further include a second reagent layer. The reagent layer is incorporated with the immobilized reagent which comprises an immobilized form of the analyte which is not capable of being solubilized or otherwise removed from the reagent layer upon contact with the test medium. The detection layer is incorporated with an immobilized form of a binding substance for the labeled reagent, which binding substance is similarly not capable of being solubilized or otherwise removed from the detection layer. Where a second reagent layer is employed, the first reagent layer is incorporated with the labeled reagent which is solubilized by the test medium when applied thereto, and the second reagent layer is incorporated with the immobilized form of the analyte.

It is to be appreciated that according to the teachings of the present invention, the layers which comprise the test device are in fluid contact with one another whereby the layers of the test device which are associated with each other permit the diffusion of a fluid into and between these layers. Such fluid contact permits passage of at least some components of a fluid sample, e.g., antigens, haptens, and/or antibodies, between the layers of the device and is preferably uniform along the contact interface between the fluid contacting layers. Accordingly, upon application of the liquid test medium and labeled reagent to the reagent layer, the liquid test medium and labeled reagent are permitted to diffuse and permeate into and through the reagent layer and into the detection layer. Where a first and second reagent layer are provided, the liquid test medium is similarly permitted to diffuse and permeate into and through the first reagent layer whereby the labeled reagent incorporated therein is solubilized and the liquid test medium and the labeled reagent further diffuse and permeate into and within the second reagent layer and into and within the detection layer.

Once the liquid test medium and the labeled reagent have been applied to and permeate the reagent layer as heretofore described, if the analyte being detected is present in the liquid test medium, then substantially all of the analyte present is brought into direct fluid contact with and specifically bound to the labeled reagent. As a result of the fluidity between the reagent layer and the detection layer, the resulting analyte-(labeled reagent) complex thereby formed is free to migrate within and out of the reagent layer and into the detection layer. As will be described in greater detail hereinafter, the labeled reagent preferably provides only one available binding site for binding of the analyte to the labeled reagent. As a result, once such available binding site has been occupied by analyte, the analyte-(labeled reagent) complex is free to migrate within and out of the reagent layer without being immobilized by the immobilized analyte incorporated therein. Similarly, where a first and second reagent layer are provided, upon application of the liquid test medium to the first reagent layer, the labeled reagent is solubilized and substantially all of the analyte present is brought into direct fluid contact with and specifically bound to the labeled reagent. The resulting analyte-(labeled reagent) complex thereby formed is permitted to migrate within and out of the first reagent layer, through the second reagent layer, and into the detection layer. Any of the labeled reagent which does not become bound to analyte from the test medium is bound to and immobilized by the immobilized analyte in the reagent layer, or, where a first and second reagent layer are provided, immobilized in the second reagent layer.

It is to be appreciated that according to the teachings of the present invention, once the analyte-(labeled reagent) complex migrates into the detection layer, the complex becomes specifically bound to and immobilized by a binding substance for the labeled reagent which is immobilized in the detection layer. As will be described in greater detail hereinafter, the labeied reagent includes a chemical group having a detectable physical property, which, upon binding to the analyte from the liquid test medium and migration into the detection layer, can be detected, measured and correlated to the amount of analyte in the liquid test medium. Accordingly, immobilization of the analyte-(labeled reagent) complex in the detection layer prevents migration of the complex out of the detection layer and into the reagent layer(s) and permits the accurate and sensitive detection and measurement of all of the labeled reagent bound to analyte from the test medium in the detection layer.

Labeled Reagent and Detection Systems

According to the teachings of the present invention, the labeled reagent comprises a chemical group having a detectable physical property and a binding site for the binding substance immobilized in the detection layer. It is to be appreciated that the immobilized binding substance in the detection layer does not participate in the initial binding reaction among the analyte, labeled reagent, and immobilized reagent. Accordingly, selection of an appropriate binding substance for immobilization in the detection layer necessarily depends upon the selective recognition for such binding site by the binding substance. Preferably, the labeled reagent comprises a ligand moiety which forms a specific binding pair with the binding substance. In particular, preferred representative binding pairs for the ligand moiety and the binding substance include such binding pairs as haptens and antibodies, or fragments thereof, to such haptens; biotin and avidin; carbohydrates and lectins; and antibody, or fragment thereof, having an intact binding site for Protein A and Protein A; and the like. Additional binding pairs include complementary single stranded oligonucleotide sequences; effector molecules and receptor pairs; prosthetic groups and apoprotein; enzyme cofactors and enzymes; polymeric acids and bases; dyes and protein binders; peptides and specific protein binders (e.g., ribonuclease, S-peptide and ribonuclease S protein); enzyme inhibitors (reversible and irreversible), enzymes and the like.

Further, the labeled reagent can be selectively immobilized by binding to an adsorbent material for the labeled reagent, such as an ion exchange material, which acts as the binding substance which is immobilized in the detection lever. Other materials may also be employed as the binding substance of the present invention provided, of course, that the binding site on the labeled reagent and the binding substance have selectivity for binding each other and would not be subject to substantial nonspecific binding to other reagents within the assay system.

The detectable chemical group of the labeled reagent will be a substance which has a detectable physical property. Such substances have been well developed in the field of immunoassays and in general most any such label employed in immunoassays can be applied to the labeled reagent of the present invention.

In particular, chemical groups having detectable physical properties are those groups which are detected on the basis of their own physical properties which do not require a chemical reaction with another chemical or substance to provide a detectable signal. Such groups principally include fluorescers such as umbelliferone, fluorescein, resorufin, various rhodamines, dansyl derivatives, and aminonaphthalenesulfonic acid, (see Clin. Chem. (1979) 25:353), phosphorescent molecules such as pyrene, chromophores such as para- or ortho-nitrophenol, phenolpthalein, napthol AS, paranitroanilide and thymolpthalein, radioisotopes such as $^3H$, $^{35}S$, $^{32}P$, $^{125}I$ and $^{14}C$, spin labels including nitroxide radicals such as DOXYL, PROXYL and TEMPO derivatives; or electroactive moieties such as protons, fluoride, oxygen, ammonia and hydrogen peroxide Once the appropriate binding reactions have taken place as heretofore described, the resulting labeled reagent which migrates into the detection layer is bound to and immobilized by the appropriate binding substance for the labeled reagent which has been immobilized therein. Accordingly, immobilization of the complex results in a localized or concentrated signal which is provided by the chemical group of the labeled reagent in the detection layer and from which the detectable signal provided thereby is detected and measured. It is to be appreciated that the inherent physical property or characteristic of such label having a detectable physical property obviates the need for incorporating a chemical reactant or interactive substance in the detection layer since the signal is produced and thereby detectable without a chemical reaction or interaction with an interactive substance.

The detectable signal is preferably measured by passing the test device through a zone which is provided with suitable apparatus for detecting the ultimate optical signal such as by reflection, transmission or fluorescence photometry. Such apparatus, for example, directs a source of energy, such as light, on and/or into the test device element. The light is then reflected from the element back to a detecting means where a reflective support is employed, or passes through the element to a detector in the case of transmission detection where a radiation-transmissive or transparent support is employed. Conventional techniques of fluorescence spectrophotometry or luminescence measurements can also be employed if desired. In techniques where an electroactive species are used as a label, detection can be accomplished with ampometric or potentiometric detection devices.

Multilayer Analytical Elements

Figure 1:
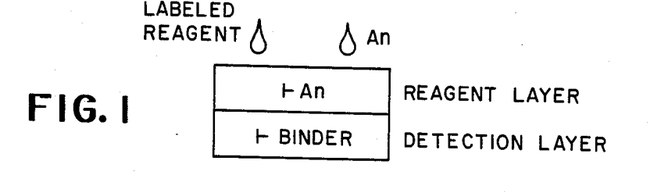
FIG. 1 is a sectional view of a multilayer test device having a reagent layer and a detection layer constructed according to the present invention.

Referring now to the drawings, FIG. 1 illustrates one embodiment of the multilayer test device of the present invention which comprises at least one reagent layer and a detection layer which are in fluid contact with one another. The reagent layer is incorporated with the immobilized form of the analyte (represented as " An"), and the detection layer is incorporated with an immobilized form of a binding substance for the labeled reagent (represented as " Binder") as heretofore described.

Upon application of both the liquid test medium containing analyte and the labeled reagent to the reagent layer, the test medium and labeled reagent diffuse into the reagent layer and are thereby brought into fluid contact with the immobilized analyte in the reagent layer. In this embodiment, the labeled reagent and the test medium can be applied independently or together as a mixture, the latter being preferred since such provides equal competition between the labeled reagent and the analyte from the test medium for binding to the immobilized analyte. Accordingly, any of the analyte present in the liquid test medium becomes bound to the binding partner for the analyte of the labeled reagent and the resulting complex thereby formed is free to migrate within and out of the reagent layer and into the detection layer. Any of the excess labeled reagent which does not become bound to analyte from the test medium becomes bound to the immobilized analyte in the reagent layer through the binding partner of the analyte of the labeled reagent and prevented from migrating into the detection layer.

Alternatively, as is known in the art, rather than adding the labeled reagent as a separate component, whether by addition with the liquid test medium or by being incorporated in a separate reagent layer as described in more detail below, the labeled reagent can be prebound to the immobilized reagent in the reagent layer. Since the binding will be reversible, the presence of analyte will reverse some of such binding to release a detectable amount of the labeled reagent.

It is to be appreciated that according to the teachings of the present invention, the binding partner for the analyte preferably has only one specific binding site for the analyte. Preferably, such binding partner is a monovalent fragment of an antibody prepared against the analyte and which is purified or derived from a monoclonal antibody.

Such monovalent antibody fragments can be readily prepared by digestion of normal whole IgG antibody with a proteolytic enzyme, such as papain, to produce antibody fragments commonly referred to in the art as Fab fragments. Alternatively, such monovalent antibody fragments can also be prepared by digestion of normal whole IgG antibody with a proteolytic enzyme such as pepsin, followed by chemical reduction to produce antibody fragments commonly referred to in the art as Fab' fragments.

However, other binding partners can also be used, preferably of course having only one specific, available binding or recognition site for the analyte under determination. Such other binding partners include whole antibody hybrids, receptor molecules, and the like. For example, a whole antibody hybrid can be used which can be obtained from a number of procedures. Such hybrids can be prepared in vivo from a monoclonal cell line produced by hybridization between a secreting myeloma cell and a splenic cell which secretes the antibody of interest. The resulting cell line can spontaneously produce hybrid molecules consisting of one binding subunit with the specificity of interest and a second subunit with a specificity which is defined by the myeloma cell line. Such antibody can be isolated from homogeneous dimers of the original myeloma antibody or splenic cell by conventional protein purification techniques known in the art. Hybrids can also be chemically formed by co-mixing anti-analyte antibody with a second antibody under appropriate denaturing conditions, such as by the addition of urea (8 Molar) and reducing agents such as dithiothreitol, followed by removal of the denaturing agent to permit reconstitution of the antibody hybrids. Accordingly, a portion of the reconstituted sample will contain hybrids with a binding site for the second carrier antibody which can be further purified by conventional protein purification techniques known in the art.

Accordingly, once the analyte from the test medium has become bound to the monovalent binding partner thereof of the labeled reagent, e.g., the monovalent fragment of the antibody to the analyte, nonspecific immobilization of the resulting complex by the immobilized analyte in the reagent layer is prevented as a result of the unavailability of a binding site on the labeled reagent for the immobilized analyte. Upon migration of the analyte-(labeled reagent) complex into the detection layer, the labeled reagent becomes bound to and is immobilized by the immobilized binding substance therefor. The binding interaction of the analyte-(labeled reagent) complex with the immobilized binding substance concentrates or localizes the signal provided by the label of the labeled reagent in the detection layer for the detection and measurement thereof either visually or with the use of an appropriate instrument.

As will be described in greater detail hereinafter, except for reflecting layers and radiation-blocking agents, the various zones or layers and supports of the present invention are radiation-transmissive in most instances. Such zones or layers and supports permit effective passage of visible light, fluorescent or luminescent emission, radioactive radiation, and the like. The choice of a particular radiation-transmissive material will depend upon the particular radiation selected for use with an element in which the material is to be incorporated. Accordingly, the test device as heretofore described permits detection of the signal produced by either the immobilized labeled reagent in the reagent layer or the immobilized analyte-(labeled reagent) complex in the detection layer. As a result, the signal produced thereby, e.g., fluorescence or color, can be detected, measured and correlated to the amount of analyte present in the liquid test medium. However, the presence of the labeled reagent in both the reagent layer and the detection layer would result in detection of the signals produced from both layers, regardless from which direction the signal is detected, i.e., detected with an appropriate instrument directed at the reagent layer or the detection layer, such signals being indistinguishable from each other. It is therefore desirable to use either radiation-blocking agents incorporated into a particular layer or a reflective or radiation-blocking layer between one or more layers of the device.

In particular, as applied to the multilayer device of the present invention, a radiation-blocking layer would be positioned between the reagent layer and the detection layer of the device illustrated in FIG. 1. By incorporating such layer between the reagent layer and the detection layer, any signal produced from the immobilized labeled reagent in the reagent layer would be detected without an interfering signal produced by the immobilized analyte-(labeled reagent) complex in the detection layer as a result of such non-transmissive layer incorporated therebetween. In this manner, the signal produced by each layer can be detected, measured, and correlated to the amount of analyte in the liquid test medium without an interfering signal produced by the other layer.

Alternatively, it may be desirable to utilize radiation-blocking agents which would be incorporated into either the reagent layer or the detection layer. Opacifying pigments, such as titanium dioxide, barium sulfate or zinc oxide can be used for this purpose. Blush polymers can also be used, either independently, or incorporated with pigment to enhance radiation-blocking or other properties. Such radiation-blocking layers and agents are known in the art and include those described in U.S. Pat. Nos. 4,042,335 and 4,255,384.

Where a fluorophore is used as the label in the labeled reagent, the detectable signal can be alternatively masked from the detection system by the use of quenching phenomena without the need for radiation-blocking layers or materials. Those layers or zones in which the signal is to be blocked, e.g., the reagent layer when measuring in the detection layer, can be incorporated with an immobilized substance that effectively quenches the fluorescence of the label as a result of changes in media polarity or incorporation of quenching groups such as heavy atoms, e.g., $I^-$.

Detection of the signal produced by the labeled reagent from either the reagent layer of the detection layer can be accomplished with the use of an appropriate instrument, such as a spectrophotometer, reflectometer, fluorometer or luminometer. For example, where detection is based upon absorbance or fluorescence, an energy source from such instrument is directed either at and through the reagent layer or at and through the detection layer. On the other hand, where detection is based upon luminescence, an appropriate instrument which detects such luminescence without the need of an energy source is utilized.

Figure 2:
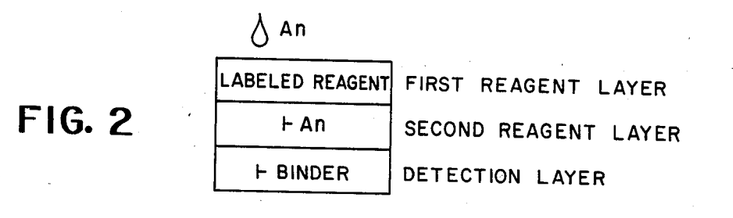
FIG. 2 is a sectional view of a multilayer test device having two reagent layers and a detection layer constructed according to the present invention.

Referring now to FIG. 2 of the drawings, a test device is illustrated that is similar to the test device of FIG. 1. In this embodiment, the test device further includes a second reagent layer positioned between the first reagent layer and the detection layer. The additional reagent layer permits incorporation of a test medium soluble form of the labeled reagent therein which obviates the need for pre-mixing the liquid test medium and the labeled reagent prior to the application thereof to the test device or the independent application thereof, such as with the test device illustrated in FIG. 1. In particular, the first reagent layer is incorporated with the test medium soluble labeled reagent, (represented as "Labeled Reagent"), which is solubilized upon fluid contact with the liquid test medium which diffuses therein. The second reagent layer is incorporated with the immobilized form of the analyte (represented as " An"), and the detection layer is incorporated with the immobilized form of the binding substance for the labeled reagent (represented as " Binder") as heretofore described.

Upon application of the liquid test medium to the first reagent layer, the liquid test medium diffuses into the first reagent layer bringing any analyte from the test medium into direct fluid contact with the labeled reagent therein while, at the same time, solubilizing the labeled reagent. Accordingly, any analyte from the test medium becomes bound to the binding partner thereof of the labeled reagent and the analyte-(labeled reagent) complex thereby formed migrates within and out of the first reagent layer and into the second reagent layer. It is to be appreciated that any of the unbound labeled reagent in the first reagent layer, i.e., excess labeled reagent, will also migrate within and out of the first reagent layer and into the second reagent layer. Since the binding site of the monovalent binding partner for the analyte of the labeled reagent has been occupied by binding to the analyte from the test medium, once within the second reagent layer, the analyte-(labeled reagent) complex is permitted to migrate within and out of the second reagent layer without becoming immobilized, and into the detection layer. Once within the detection layer, the labeled reagent becomes bound to and is immobilized by the immobilized binding substance incorporated therein to localize the signal provided by the label of the labeled reagent as heretofore described. However, since the unbound labeled reagent in the second reagent layer has an available binding site for the immobilized analyte in the second reagent layer, the labeled reagent becomes bound thereto and immobilized .thereby and prevented from further migrating into the detection layer. The resulting signal provided by the label of the immobilized analyte-(labeled reagent) complex is then detected, measured and correlated to the amount of analyte from the test medium as heretofore described.

Although the various layers of the multilayer device of the present invention can be self-supporting, it is preferred that such layers be coated or otherwise positioned onto a support member. The support member is transparent to light or other energy and will be compatible with the intended mode of signal detection. For example, where the chemistry of the test device generates a gaseous product for detection thereof with a gas sensing electrode, the support member is a fluid permeant layer in liquid contact with such electrode. Preferred support members include transparent support materials capable of transmitting electromagnetic radiation of a wavelength within the region between about 200 nm and about 900 nm. The support need not, of course, transmit over the entire 200–900 nm region, although for fluorometric detection of analytical results through the support it is desirable for the support to transmit over a wider band or, alternatively, to transmit at the excitation and emission spectra of the fluorescent materials used for detection. It may also be desirable to have a support that transmits over a narrow wavelength band width and which has reduced transmittance to adjacent wavelengths. This could be accomplished, for example, by impregnating or coating the support with one or more colorants having suitable absorption characteristics.

A radiation-transmissive or transparent support member permits a beam of energy, such as light, to pass therethrough. The beam is then reflected, such as from a radiation-blocking layer, back to a sensing component of the instrument.

Figure 3:
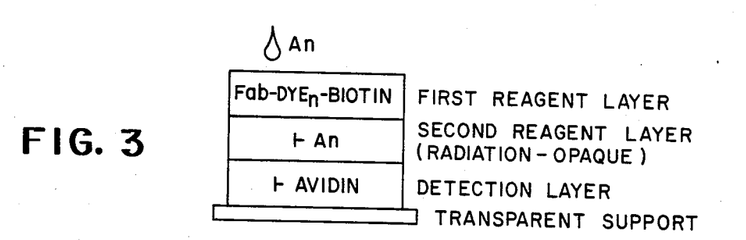
FIG. 3 is a sectional view of a multilayer test device having two reagent layers, a detection layer, and a support constructed according to the present invention.

For example, there is illustrated in FIG. 3 a multilayer test device constructed according to the teachings of the present invention having first and second reagent layers and a detection layer mounted or otherwise positioned onto a radiation-transmissive support member through which an energy source is directed. The first reagent layer is incorporated with the liquid test medium soluble labeled reagent comprising a monovalent antibody fragment of an antibody to the analyte under determination, labeled with a number of dye molecules and having biotin linked thereto as the binding moiety (represented as "Fab-Dye$_n$-Biotin"). The second reagent layer is incorporated with an immobilized form of the analyte (represented as " An"), and the detection layer is incorporated with an immobilized form of avidin (represented as " Avidin") as the binding substance for the biotin binding moiety of the labeled reagent. The immobilized avidin is incorporated in an excess amount relative to the labeled reagent so that substantially all of the analyte-(labeled reagent) complex which migrates into the detection layer is immobilized. Upon application of the liquid test medium containing analyte to the first reagent layer, the analyte therefrom is brought into direct fluid contact with the labeled reagent and becomes bound to the monovalent antibody fragment of the antibody to the analyte thereof. The analyte-(antibody fragment)-biotinylated dye complex formed thereby migrates within and out of the first reagent layer, through the second reagent layer and into the detection layer where the complex is immobilized therein by binding of the biotin binding moiety to the immobilized avidin binding substance therein. Accordingly, as heretofore described, once the analyte from the test medium has become bound to the monovalent antibody fragment of the labeled reagent, nonspecific immobilization of the resulting complex by the immobilized analyte in the second reagent layer is prevented as a result of the unavailability of a binding site on the labeled reagent for the immobilized analyte. Any of the unbound labeled reagent, however, which migrates into the second reagent layer is immobilized therein by binding of the monovalent antibody fragment of the labeled reagent to the immobilized analyte.

Since any of the labeled reagent which does not become bound to the analyte from the test medium will be immobilized in the second reagent layer, it is necessary to prevent detection of the interfering signal produced therefrom when detecting the signal produced by the labeled reagent complex immobilized in the detection layer. This is accomplished by incorporating a radiation-blocking substance into the second reagent layer, or, alternatively, interposing a radiation-blocking layer between the second reagent layer and the detection layer. Accordingly, when a source of energy is directed from an instrument through the radiation-transmissive support member and into the detection layer, the energy is reflected back through the detection layer and support member by the radiation-blocking substance or layer and thereby affected only by the label which is present in the detection layer. A radiation-blocking substance or layer is particularly desirable when the liquid test medium includes a colored substance, such as red blood cells where the liquid test medium is whole blood, in which case the radiation-blocking substance or layer prevents interference of the coloration of red blood cells which would be filtered out and remain in a layer above the detection layer.

It is to be appreciated that the various layers of the multilayer test device of the present invention are not limited to the layers and configurations as heretofore described. Additional layers for use with the multilayer test device have been described and are known in the art which enhance and/or modulate the performance of such test devices. For example, a spreading zone or layer could be included which would be positioned immediately above and adjacent to the first reagent layer. The spreading zone meters and evenly distributes an applied liquid test sample to the underlying first reagent layer. Such spreading zones or layers are known in the art and include those described in U.S. Pat. Nos. 3,992,158 and 4,427,632.

The device can also include an intermediate zone or layer between the various layers which serves as an adhesive or subbing layer to facilitate adhesion between the layers and to further facilitate adhesion of the layers to a solid support member. Intermediate zones or layers can also be employed which, for example, contain reagents for removing interferants which may prevent detection of some of the analyte or, can be a radiation-blocking zone or layer which masks zones or layers of the device to prevent interference in detection of the product. Such radiation-blocking layers can also be employed which mask the presence of various interfering substances found in test samples, such as red blood cells in whole blood.

It is also sometimes preferred to provide a timing zone or layer which controls the rate of diffusion of the various reagents incorporated into the multilayer test device through the various layers thereof. Such timing zones or layers are incorporated into the test device in order to provide controlled incubation times and sequential reactions or to facilitate manufacture of the device by preventing premature interaction of the reagents in the device.

Figure 4:
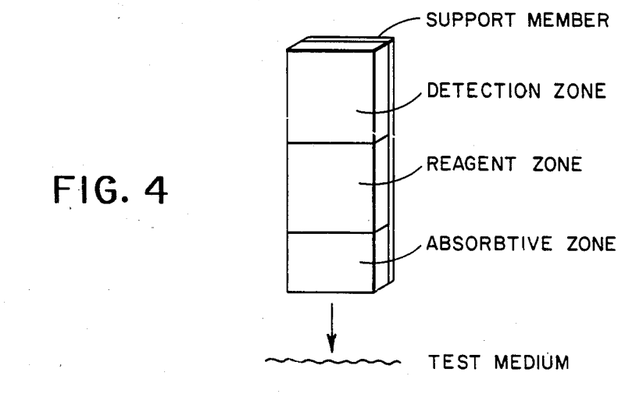
FIG. 4 is a perspective view of a chromatographic test device having an absorbtive zone, a reagent zone and a detection zone mounted onto a support member according to the present invention.
Figure 5:
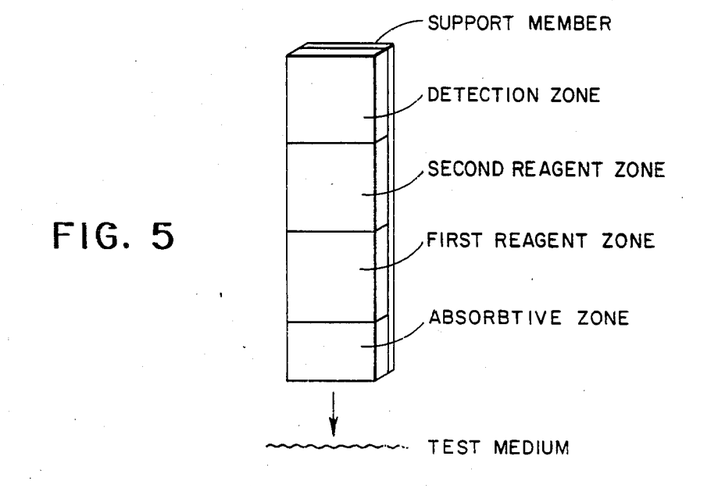
FIG. 5 is a perspective view of a chromatographic test device having an absorbtive zone, two reagent zones and a detection zone mounted onto a support member according to the present invention.

The device of the present invention can also be a multizone device having reagent zones, detection zones, and the like assembled in a configuration particularly adapted for chromatographic analysis. Such a device would include an absorbant region which would be immersed into the liquid test medium wherein the test medium would diffuse in an upward direction into the various zones.

The zones of such multizone device can be in the form of reagent pads which are mounted onto a plastic support member adapted to be immersed or dipped into a liquid test medium. The zone-forming reagent pads are positioned onto the support member in an end to end relationship wherein the ends thereof are in fluid flow contact with one another. In particular, such reagent pads include a lowermost, liquid test medium-absorbtive pad or zone, first and second reagent pads or zones, respectively, positioned thereabove, and a detection pad or zone positioned above the second reagent zone.

It is to be appreciated that the reagent and detection zones are incorporated with the various reagents of the multilayer device previously described and perform the same functions thereof. In this embodiment, however, instead of a liquid test medium sample being applied to the device, the lowermost absorbtive pad of the multizone device is immersed into the liquid test medium. In this manner, the absorbtive pad serves as a wick for the absorption of the test medium and the upward diffusion thereof into the first reagent zone, the second reagent zone, and the detection zone, respectively. Devices in configurations such as described in U.S. Pat. Nos. 4,301,139 and 4,361,537 which use a developing fluid can also be adapted to the present invention. As was previously described, analyte from the test medium which diffuses into the first reagent zone binds to the labeled reagent incorporated therein and the complex formed thereby continues to migrate through the second reagent zone and into the detection zone where the analyte-(labeled reagent) complex becomes bound to and is immobilized by the immobilized binding substance immobilized therein to thereby localize the signal provided thereby for the further detection and measurement thereof. Similarly, any of the labeled reagent in the first reagent zone which is not bound by analyte from the test medium migrates into the second reagent zone where it is immobilized by the immobilized form of the analyte incorporated therein.

According to the teachings of the present invention, the various layers described herein preferably comprise a porous matrix which is permeable to at least some components of a fluid sample, e.g., antigens, haptens and/or antibodies, such permeability generally arising from porosity, ability to swell or any other characteristic. The matrix material can include various porous fibrous materials such as cellulose, papers, fleeces, felts, woven fabrics and the like, whether formed from natural or synthetic materials. Such materials, for example, are described in U.S. Pat. Nos. 3,802,842; 3,809,605; 3,897,214 and 3,987,213. Other porous, but nonfibrous materials include microporous polymers such as those referred to in U.S. Pat. No. 3,552,929.

Preferably, the matrix-forming materials of the various layers of the multilayer test device of the present invention are permeable materials such as gelatin, agarose and the like. Such materials permit the passage of fluids by diffusion, rather than by capillary flow as with fibrous, porous materials such as papers or woven materials. Although the porous, fibrous materials described above can be used, gelatin, agarose and the like are particularly preferred because of their uniform permeability to liquids, as well as their ability to permit the passage of light or other electromagnetic radiation therethrough. Knowing the liquid test medium under analysis, the choice of an appropriate material will be apparent to one skilled in the art.

Various methods known in the art are available for the immobilization of analyte in the test device of the present invention, or, a derivative or suitable analog of the analyte can be prepared in order to facilitate the immobilization thereof into the test device. Although immobilization through covalent attachment of the analyte or analog thereof is preferred, other means which utilize non-covalent association such as ion exchange or adsorption can also be used. Immobilization of analyte can be achieved, for example, by direct incorporation into the carrier matrix of the device, such as cellulose in paper, or into gelatin or agarose in films. Alternatively, the analyte analog can be linked to a polymeric carrier which is then subsequently incorporated into the matrix of the device, the polymer being of sufficient size to prevent significant diffusion between the binding and detection layers. In gelatin, for example, polymers greater than 10,000 in molecular weight will exhibit negligible diffusion through the gelatin matrix. Similarly, in agarose, polymers greater than two million in molecular weight will be restricted from diffusing through the matrix. The analyte can also be linked directly or through a polymer backbone to very small particles such as polystyrene microbeads which can then be subsequently incorporated into the matrices of the device. Such particles are readily available in a range of sizes and include polystyrene, microcrystalline cellulose, cross-linked dextrans and cross-linked agaroses, ion exchange resins, and the like. A wide range of chemistries are available to couple the agents onto the carrier. For example, water soluble carbodiimides can be used to activate free carboxyl groups for subsequent reaction with nucleophiles including various amine compounds; amide residues or beads can be converted by reaction with hydrazine to hydrazides which can be further reacted with bifunctional reagents such as glutaraldehyde, 1,5-difluoronitrobenzene, 4,4'-difluoro-3,3'-dinitrophenyl sulfone, 2,4-dichloro-6-carboxymethyl-amino-5-triiazine, dimethyladipimidate or dimethylsuberimidate, and the like, followed by reaction with amines or other nucleophiles linked to the analyte or analog of interest; hydrazides can be converted to azide groups by reaction with nitrous acid through a diazotization reaction; hydrazides can be reacted with succinic anhydride to incorporate carboxylate groups with a spacer arm; aliphatic amines or particles can also be reacted with bifunctional reagents analogous to the hydrazide chemistry, including the use of heterobifunctional crosslinkers which allow attachment to the amines of functional groups with differing specificities such as a maleimide group which shows enhanced specificity for sulfhydryl derivatives; hydroxyl groups can be activated by cyanogen bromide, tosyl chloride, carbonyl diimidazole, or p-nitrophenylchloroformate; particles such as polystyrene can be nitrated, the nitro groups reduced to aromatic amines, and the aromatic amines can be diazotized prior to reaction with a nucleophilic-analyte/analog of interest. Nitrocellulose, diazobenzoxymethyl (DMB) paper, derivatized nylon mesh, or paper activated with cyanogen bromide, p-nitrophenylchloroformate, or carboxyldiimidazole can also be utilized to link nucleophile reagents or reagents linked to reactive polymers.

As an alternative to directly binding the appropriate binding reagent to a material immobilized in the reagent layer, one can also take advantage of specific binding partners to obtain the necessary immobilization in situ during performance of the assay. The material to be immobilized, i.e., the analyte or analog or binding partner, can comprise or be modified to comprise a binding site for a distinct binding substance which in turn can be immobilized in the reagent layer. The immobilizable material thus can be situated in any convenient location in the device and upon performance of the assay will result in the appropriate immobilization. Binding interactions such as described previously for immobilizing the labeled eagent in the detection layer can be used. Similarly, the methods described above for the immobilization of analyte can also be generally applied for immobilization of the various detection reagents or derivatives thereof.

The test device of the present invention utilizes multiple reagent layers which are assembled to permit fluid contact between adjacent layers as heretofore described. The various layers can be prepared using film formers to prepare consecutive over-laying coatings or prepared by superimposing layers of fibrous reagent matrix such as a filter paper, glass fiber or woven polyester. Alternatively, adjacent zones can be configured into a chromatography format with each zone attached on the support member with the edges of each reaction zone being in direct fluid contact as heretofore described.

Multiple layers of paper, for example, can be held in juxtaposition with an enclosing plastic frame, or alternatively with a liquid permeant mesh screen, or by incorporation of a water-soluble adhesive between the layers. The casting of multilayer films can be accomplished by a number of techniques in the art for casting films, including the use of a doctor blade, extrusion coater, Meyer rod, puddle coater or gravure coater. Alternatively, multiple consecutive layers can be cast with a cascade coater. Film layers formed by the above procedures can be overlayed with a fabric or mesh material containing reagents which is incubated for a predetermined period of time.

Analyte

The present assay can be applied to the detection of any analyte for which there is a binding counterpart available. The analyte usually is a peptide, polypeptide, protein, carbohydrate, glycoprotein, steroid, nucleic acid or other organic molecule for which a binding counterpart exists or which is producible in biological systems or can be synthesized. The analyte, in functional terms, is usually selected from the group comprising antigens and antibodies thereto; haptens and antibodies thereto; complementary polynucleotide sequences; and hormones, vitamins, metabolites and pharmacological agents, and their binding counterparts. Usually, the analyte is an immunologically-active polypeptide or protein, usually having a molecular weight of between about 1,000 and about 10,000,000, such as an antibody or antigenic polypeptide or protein, or a hapten having a molecular weight of at least about 100, and usually less than about 1,500.

Representative polypeptide analytes are angiotensin I and II, C-peptide, oxytocin, vasopressin, neurophysin, gastrin, secretin, bradykinin, and glucagon.

Representative protein analytes include the classes of protamines, mucoproteins, glycoproteins, globulins, albumins, scleroproteins, phosphoproteins, histones, lipoproteins, chromoproteins, and nucleoproteins. Examples of specific proteins are prealbumin, $\alpha_1$-lipoproteins, human serum albumin, $\alpha_1$-acid glycoprotein, $\alpha_1$-antitrypsin, $\alpha_1$-glycoprotein, transcortin, thyroxine binding globulin, haptoglobin, hemoglobin, myoglobulin, ceruloplasmin, $\alpha_2$-macroglobulin, $\beta$-lipoprotein, erythropoietin, transferrin, hemopexin, fibrinogen, the immunoglobulins such as IgG, IgM, IgA, IgD, and IgE, and their fragments, e.g., $F_c$ and $F_{ab'}$ complement factors, prolactin, blood clotting factors such as fibrinogen, thrombin and so forth, insulin, melanotropin, somatotropin, thyrotropin, follicle stimulating hormone, leutinizing hormone, gonadotropin, thyroid stimulating hormone, placental lactogen, instrinsic factor, transcobalamin, serum enzymes such as alkaline phosphatase, lactic dehydrogenase, amylase, lipase, phosphatases, cholinesterase, glutamic oxaloacetic transaminase, glutamic pyruvic transaminase, and uropepsin, endorphins, enkephalins, protamine, tissue antigens, bacterial antigens, and viral antigens such as hepatitis associated antigens (e.g., $HB_sAg$, $HB_cAg$ and $HB_eAg$).

Representative hapten analytes include the general classes of drugs, metabolites, hormones, vitamins, toxins and the like organic compounds. Haptenic hormones include thyroxin and triiodothyronine. Vitamins include vitamins A, B, e.g., $B_{12}$, C, D, E and K, folic acid and thiamine. Drugs include antibiotics such as aminoglycosides, . e.g., gentamicin, tobramycin, amikacin, sisomicin, kanamycin, and netilmicin, penicillin, tetracycline, terramycin, chloromycetin, and actinomycetin; nucleosides and nucleotides such as adenosine diphosphate (ADP) adenosine triphosphate (ATP), flavin mononucleotide (FMN), nicotinamide adenine dinucleotide (NAD) and its phosphate derivative (NADP), thymidine, guanosine and adenosine; prostaglandins; steroids such as the estrogens, e.g., estriol and estradiol, sterogens, androgens, digoxin, digitoxin, and adrenocortical steriods; and others such as phenobarbital, phenytoin, primidone, ethosuximide, carbamazepine, valproate, theophylline, caffeine, propranolol, procainamide, quinidine, amitryptiline, cortisol, desipramine, disopyramide, doxepin, doxorubicin, nortryptiline, methotrexate, imipramine, lidocaine, procainamide, N-acetylprocainamide, amphetamines, catecholamines, and antihistamines. Toxins include acetyl T-2 toxin, alfatoxins, cholera toxin, citrinin, cytochalasins, staphylococcal enterotoxin B, HT-2 toxin, and the like.

Liquid Test Medium

The liquid test medium containing the analyte under determination can be a naturally occurring or artifically formed liquid suspected to contain analyte, and is usually a biological fluid or a dilution thereof. Biological fluids from which analyte can be determined include serum, whole blood, plasma, urine, saliva, and amniotic and cerebrospinal fluids.

The present invention will now be illustrated, but is not intended to be limited, by the following examples:

EXAMPLE 1

Preparation of Dye/Biotin Labeled Antibody

Ascites fluid containing an anti-digoxin antibody (~6 mg/mL) is diluted five-fold in 0.1M citrate buffer, pH 3.5 and incubated with a 1:50 (w/w) pepsin:antibody solution for 48 hours at 37° C. After concentration to ~5 ml by ultrafiltration over an Amicon PM30 membrane (Amicon Corp., Danvers, MA, USA), the sample is gel filtered on a Sephacryle ®S-300 (Pharmacia, Inc., Piscataway, NJ, USA) column (2.4×90 cm) and equilibrated with 50 mM sodium phosphate and 0.10M sodium chloride (pH 7.6) to isolate the F(ab')$_2$ fragment of the antibody. The antibody is reduced with 3 mM dithiothreitol for 45 minutes, followed by the addition of 4 mM iodoacetamide (final concentration) for 1 hour to alkylate free sulfhydryl groups. The protein peak is pooled after desalting on a P-6DG polyacrylamide gel resin (Bio. Rad. Co., Richmond, CA).

An aliquot of the pooled protein is reacted for 2 hours with a five-fold molar excess of N-hydroxysuccinimide aminobiotin (Pierce Chemical Co., Rockford, IL). The reaction product is then desalted on a P-6DG column and concentrated to 1 mg/mL protein by ultrafiltration over an Amicon PM30 membrane.

An aliquot of protein is then reacted overnight with a twenty-fold molar excess of tetramethyl rhodamine-8-isothiocyanate (Research Organics, Inc., Cleveland, OH) previously dissolved in dimethylsulfoxide. The reaction product is passed over an immobilized avidin column (Pierce Chemical Co.) previously equilibrated with 0.1M sodium phosphate and 0.5M sodium chloride (pH 7.8). The bound protein is eluted with 0.2M sodium acetate, 0.5M sodium chloride (pH 4.0), then followed by gel filtration on a P-6DG column (equilibrated with 20 mM sodium phosphate, 100 mM sodium chloride [pH 7.2]and the protein peak collected.

EXAMPLE 2

Preparation of the Immobilized Analyte Layer

Whatman 31-ET (Whatman, Inc., Clifton, NJ, USA) paper is activated for subsequent derivatization with para-nitrophenylchloroformate (NPCF). Paper sheets are immersed for fifteen minutes in distilled water and the water is then decanted and the paper rinsed with six successive volumes of acetone to remove free water. The paper is then immersed in a 10% solution of NPCF in acetone, incubated for six hours, and then unreacted NPCF removed by successive rinses with acetone. The rinse solution is tested for the presence of the formate by adding 100 $\mu$L of 1N NaOH to 300 $\mu$L of the rinse solution. The rinsing is continued with three volumes of acetone until there is no detectable yellow color, followed by washing with 1 L of distilled water and subsequently washed with 5×100 mL volumes of acetone, and the solvent removed by air drying.

EXAMPLE 3

Preparation of Immobilized Binding Layer

Whatman 54 paper (3.7 g) is incubated with 2 g of 1,1'-carbonyldiimidazole in 100 mL of acetone for one hour at room temperature with occasional stirring. The paper is washed with 3×200 mL volumes of acetone and dried at 50° C. for approximately ten minutes (or until there is no detectable acetone odor) and stored with silica gel desiccant at 4° C. until further use. The paper is subsequently reacted with 10 mg/ml strepavidin (Sigma Chemical Co., 54762, Sigma Chemical Co., St. Louis, MO 63178) in 50 mM sodium phosphate pH 7.4 for fourteen hours. The paper is washed extensively with 10 mM sodium phosphate buffer pH 7.4.

EXAMPLE 4

Dye/Biotin-Antibody Conjugate Layer

Whatman 31 ET paper is dipped through a solution containing 10 mg/mL of anti-digoxin Fab dye/biotin in a 0.6M sodium phosphate buffer, pH 7.4 and dried at 40° C. for twenty minutes.

EXAMPLE 5

Assembly of the Multilayer Device

A composite strip device is assembled from the three reagent elements described above. The conjugate layer is laminated onto a double-faced adhesive tape (3M Company, St. Paul, MN, USA) and cut into a 1 cm wide ×12.7 cm long ribbon. This material is then laminated onto and along the length of an edge of one surface of an 8.3 cm wide ×12.7 cm long clear polystyrene support (Trycite ®, Dow Chemical Co., Midland, MI, USA). A 1-2 mm strip of double-faced adhesive tape is mounted along the back edge of the conjugate layer and a 1 cm wide ribbon of reagent paper containing the immobilized analyte analog is mounted thereon by the strip of double-faced adhesive tape. The above method is repeated to mount the ribbon of binding layer paper containing the immobilized binding protein. The resulting multilayer device is slit into 5 mm wide ×8.3 cm long reagent strips having the various layers mounted to the ends thereof.

EXAMPLE 6

Operation of the Device

A normal human serum sample is spiked to 5 nM with digoxin. A range of concentration from 0.2 to 5.0 nM digoxin are prepared by dilution of the stock reagent with normal human serum. An 80 μL aliquot of sample is applied to the test device to initiate the test. The test device is mounted in a fluorometer which is capable of measuring a front face fluorescent measurement of the test device (e.g., Howard, W. et al., Analyt. Chem. 55 878-888 [1983]). The excitation light illuminates the surface of the device with light passing through a 540 nm interference filter (3 cavity, Ditric Optics, Inc., Hudson, MA) through a fiber optic bundle mounted at a 45° angle relative to the normal of the reagent pad. Emitted light is detected by a fiber optic bundle mounted normal to the pad which carries the light to a 570 nm interference filter (3 cavity, Ditric Optics, Inc., Hudson, MA, USA) and associated detection electronics. The change in fluorescence is measured and related to the concentration of digoxin applied.

What is claimed is:

1. A multizone test device for the specific binding assay determination of an analyte in a liquid test medium involving binding among (i) the analyte, (ii) a labeled or immobilized form of the analyte or of a binding analog thereof, and (iii) an immobilized or labeled form, respectively, of a binding partner of the analyte; the labeled one of the analyte, analog thereof, or binding partner being a labeled reagent comprising a detectable chemical group having a detectable physical property, the test device comprising, in fluid flow contact,
    (1) a reagent zone comprising a solid, porous matrix incorporated with an immobilized one of the analyte, analog thereof, or binding partner, and
    (2) a detection zone comprising a solid, porous matrix for receiving and measuring labeled reagent which migrates into said detection zone and incorporated with an immobilized form of a binding substance for the labeled reagent.

2. The test device of claim 1 wherein the labeled reagent comprises an antibody, or a fragment thereof having an intact binding site for protein A, and the binding substance for the labeled reagent immobilized in the detection zone 3. The test device of claim 1 wherein the labeled reagent is incorporated in said reagent zone and comprises a detectable chemical group, is a fluorescer or a chromophore.

4. The test device of claim 1 wherein the binding substance for the labeled reagent is immobilized in the detection zone by being covalently coupled to the matrix comprised therein.

5. The test device of claim 1 wherein the binding substance for the labeled reagent is immobilized in the detection zone by being attached to a high molecular weight polymeric substance dispersed in said matrix.

6. The test device of claim 1 wherein the binding partner for the analyte is an antibody or a fragment thereof.

7. The test device of claim 1 which comprises a solid, porous chromatographic element and wherein the reagent and detection zones are discrete sections of such element.

8. The test device of claim 1 wherein the immobilized binding substance for the labeled reagent in the detection zone is an antibody, or a fragment thereof, which binds the labeled reagent.

9. The test device of claim 8 wherein the labeled reagent comprises an antibody, or a fragment thereof, to the analyte and the binding substance for the labeled reagent immobilized in the detection zone is an antibody, or a fragment thereof, to said anti-analyte antibody or fragment thereof.

10. The test device of claim 1 wherein the immobilized binding substance for the labeled reagent in the detection zone is an adsorbent material for the labeled reagent.

11. The test device of claim 10 wherein the absorbent material is an ion exchange material.

12. The test device of claim 1 wherein the reagent and detection zones are in the form of layers in fluid flow contact.

13. The test device of claim 12 which additionally comprises a reagent layer comprising a solid, porous matrix incorporated with a test medium soluble form of the labeled reagent.

14. The test device of claim 12 which additionally comprises a support element situated on the opposite side of the detection layer from the reagent layer.

15. The test device of claim 1 wherein the labeled reagent is incorporated in said reagent zone and additionally comprises a ligand moiety and the immobilized binding substance for the labeled reagent in the detection zone is a binding partner of such ligand moiety.

16. The test device of claim 15 wherein the ligand moiety is a carbohydrate or a lectin which specifically binds therewith, and the binding partner for the ligand moiety is the other thereof.

17. The test device of claim 15 wherein the binding partner of the ligand moiety is a protein which specifically recognizes such moiety.

18. The test device of claim 17 wherein the ligand moiety is biotin or avidin, and the binding partner for the ligand moiety is the other thereof.

19. The test device of claim 17 wherein the protein which specifically recognizes the ligand moiety is an antibody or a fragment thereof.

20. The test device of claim 19 wherein the ligand moiety is a hapten.

21. In a multilayer immunoassay test device for the determination of an analyte in an aqueous liquid medium, which test device provides a detectable optical signal upon contact with aqueous medium containing analyte, the test device comprising, in fluid flow contact and in the following ordered sequence,
    (1) a first reagent layer comprising a solid, porous matrix incor-orated with a water soluble form of a labeled reagent comprising an antibody, or a fragment thereof, for the analyte and a fluorescer or chromophore label which provides the detectable optical signal, (2) a second reagent layer comprising a solid, porous matrix incorporated with an immobilized form of the analyte or a binding analog thereof, (3) a detection layer comprising a solid, porous matrix for receiving and measuring labeled reagent which migrates into such layer and incorporated with an immobilized form of a binding substance for the labeled reagent, and (4) a support element comprising a solid, nonporous substrate.

22. The test device of claim 21 wherein the binding substance for the labeled reagent immobilized in the detection zone is an antibody, or a fragment thereof, to said anti-analyte antibody or fragment thereof.

23. The test device of claim 21 wherein the binding substance for the labeled reagent is immobilized in the detection layer by being covalently coupled to the matrix comprised therein.

24. The test device of claim 21 wherein the labeled reagent comprises a monovalent anti-analyte antibody fragment.

25. The test device of claim 24 wherein the antibody fragment is derived from a monoclonal antibody.

26. The test device of claim 21 wherein the support element is transparent to the detectable optical signal.

27. The test device of claim 26 wherein the second reagent layer is opaque to the detectable optical signal.

28. The test device of claim 26 which additionally comprises an opaque layer comprising a solid, porous matrix which is opaque to the detectable optical signal and which is situated between the second reagent layer and the detection layer.

29. The test device of claim 21 wherein the labeled reagent additionally comprises a ligand moiety and the immobilized binding substance for the labeled reagent in the detection zone is a binding partner of such ligand moiety.

30. The test device of claim 29 wherein the binding partner of the ligand moiety is a protein which specifically recognizes such moiety.

31. The test device of claim 30 wherein the ligand moiety is biotin or avidin, and the binding partner for the ligand moiety is the other thereof.

32. The test device of claim 30 wherein the protein which specifically recognizes the ligand moiety is an antibody or a fragment thereof.

33. The test device of claim 32 wherein the ligand moiety is a hapten.

* * * * *